United States Patent

Borger

Patent Number: 5,578,003
Date of Patent: Nov. 26, 1996

[54] SAFETY DEVICE FOR A BLOOD-, WOUND SECRETION-OR INFUSION SUPPLYING CONDUIT, AND BLOOD-WOUND SECRETION- OR INFUSION SUPPLY SYSTEM PROVIDED THEREWITH

[76] Inventor: Ludwig Borger, Kruppstrasse 6b, 45711 Datteln, Germany

[21] Appl. No.: 523,475

[22] Filed: Sep. 5, 1995

[30] Foreign Application Priority Data

Sep. 12, 1994 [DE] Germany .......................... 44 32 348.4

[51] Int. Cl.$^6$ ...................................................... A61M 5/00
[52] U.S. Cl. .............................. 604/65; 604/131; 128/899
[58] Field of Search ................................ 604/29, 31, 65, 604/66, 131; 128/899

[56] References Cited

U.S. PATENT DOCUMENTS

| | | | |
|---|---|---|---|
| 2,979,055 | 4/1961 | DeBeer et al. | 604/66 X |
| 3,890,968 | 6/1975 | Pierce et al. | 604/65 |
| 3,942,526 | 3/1976 | Wilder et al. | 128/899 |
| 4,024,855 | 5/1977 | Bucalo | 128/899 X |
| 4,747,832 | 5/1988 | Buffet . | |
| 4,797,655 | 1/1989 | Orndal et al. | 604/31 X |
| 5,190,059 | 3/1993 | Fabian et al. | 128/899 |
| 5,445,622 | 8/1995 | Brown | 604/63 X |

FOREIGN PATENT DOCUMENTS 3344817   8/1993   Germany .

*Primary Examiner*—Sam Rimell
*Attorney, Agent, or Firm*—Michael J. Striker

[57] ABSTRACT

A safety device for blood-, wound secretion- and infusion supplying conduit which leads to a vessel inlet, the safety device comprises a magnet mountable on a conduit, a Reed-relay fixed substantially close to the magnet on a skin of a patient so that when a distance between the Reed-relay and the magnet increases as a result of moving away of the vessel input the Reed-relay is switched, and a device for triggering alarm in response to the switching of the Reed-relay. Also, a system including the vessel, the conduit and the safety device is proposed.

8 Claims, 1 Drawing Sheet

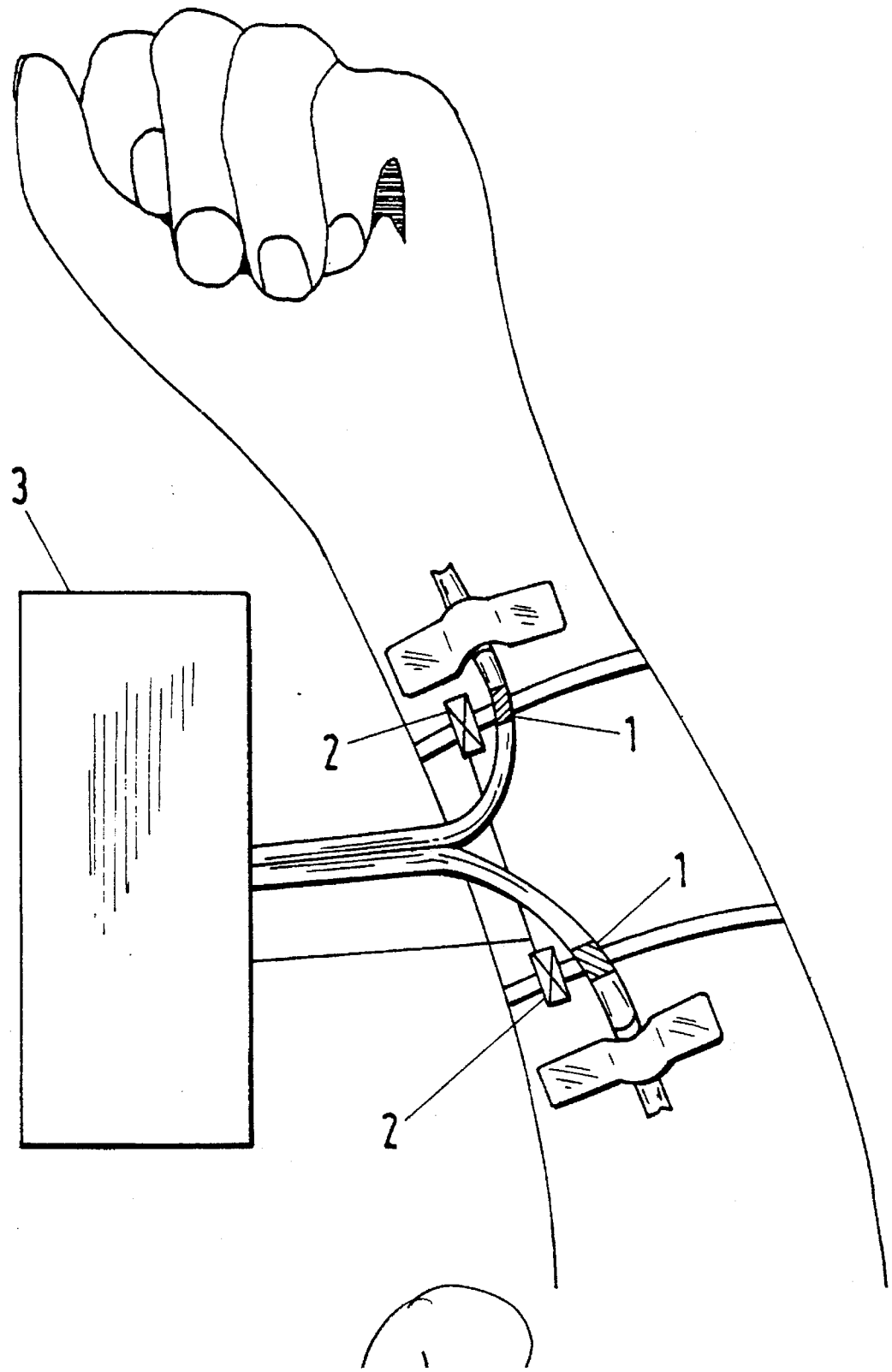

SAFETY DEVICE FOR A BLOOD-, WOUND SECRETION-OR INFUSION SUPPLYING CONDUIT, AND BLOOD-WOUND SECRETION- OR INFUSION SUPPLY SYSTEM PROVIDED THEREWITH

BACKGROUND OF THE INVENTION

The present invention relates to a safety device for blood-, wound secretion- or infusion supplying conduit which leads to a vessel inlet and blood-, wound secretion or infusion supply system provided therewith.

Safety devices of the above mentioned general type are known in the art. One of such safety devices on an infusion hose is disclosed in the German document DE 33 44 817 C2. In this device a photoelectric drop detecting device is arranged on a drop chamber, and a control device with a mechanical regulating arrangement acts on immovable lever for regulating the infusate flow by squeezing the infusion hose against an abutment. For providing a dynamically controllable, mechanical safety device for suddenly interrupting the infusate flow in the event of disturbances in the mechanical or electronic systems without indicating a current supply, it is proposed in this document to use as the safety device a rocker- or plunger-shaped actuating element which is prestressed by a spring and acts on the lever. A current excited holding magnet which counteracts the spring force holds the actuating element in an open ready position, and in the event of a drop of the magnet current brings the movable lever into a position in which it completely squeezes the infusion hose and thereby brings the infusate flow to sudden interruption. The whole safety device provides the interruption of the life sustaining infusion to the patients when certain disturbances occur. Thereby however a patient is not serviced. This safety device does not take into consideration disturbances of the infusate flow, which are caused for example by patients themselves when an infusion canula is completely or partially pulled out or pressed in. In this case the known infusion regulating apparatus adjusts the infusate flow to the changing conditions by corresponding nominal-actual value comparison, without triggering an alarm. Moreover, this known infusion regulating apparatus and its safety device must have a complicated construction which is also susceptible to corresponding disturbances.

U.S. Pat. No. 4,747,832 discloses an infusion apparatus with mechanical parts implanted under the skin of a patient and with expensive electronic parts arranged outside of the skin for infusion of intramuscular or intravenous medicaments, for example, insulin for treatment of diabetes, neuroleptic, zytostatics or other medicaments. The control of the liquid to be infused from the container is performed by magnetic elements which are arranged at both sides of the skin and set in operation from outside by a crank or an electric regulator for supplying the required infusion liquid from the supply container by an infusion pump through several regulating valves to an output of a catheter. The operation of the infusion pump is based on the law that the total infusion quantity supplied by it is equal to the sum of the partial quantity from the supply container and a further partial quantity in the catheter to be constant. However, the non-uniformities which are produced by a position displacement of the catheter or the supply conduit are not taken into consideration and do not trigger an alarm, due to displacement of the catheter. Moreover, this apparatus is always connected with an implantation of its mechanical parts, and in view of its complicated construction involving a plurality of differently designed, multi-stage gears should be considered as disturbance-prone.

An efficient safety device of the above mentioned type has not been developed yet for a long time.

In order to provide some help in this situation, the conduit which leads to or from is glued with adhesive tapes, or in the case of central vein catheters it is sewn. However, no direct technical monitoring system is provided. Therefore, displacement of canulas or catheters, which as a rule is not recognized can lead to substantial risks to the patient, such as follows:

Air embolism in case of central vein catheters;

Blood loss during transfusions or blood return;

Contamination of the vessel input.

Several examples for the above mentioned three main groups of risks are presented hereinbelow.

As for the air embolism in the case of central vein catheters, in the case of coincidence of a negative central vane pressure and a partial displacement of a central vein catheter an air embolism occurs. During air embolism the air is drawn into the circulation of the patient, it causes a displacement of the capillary regions in heart or lungs and can lead to death.

As for the blood losses, the conventional dialysis apparatuses measure the resistance between the apparatus and the patient during a return of the blood. The blood is supplied with a speed of 200–400 ml/min through a canula into the patient. The resistance of the canula constitutes a great part in the pressure monitoring region of the dialysis apparatus. In the event of displacement of the canula, the blood flows from the arterial vessel input and the dialysis apparatus outwardly of the patient. The dialysis apparatus reacts first due to secondary influences.

Finally, as for the contamination of the vessel input, the blood-, wound secretion- and infusion supplying vessel inlets can slide out. Hygienically microbial impurities can be located on these unprotected vessel inputs.

SUMMARY OF THE INVENTION

Accordingly, it is an object of the present invention to provide a safety device of the above mentioned general type, which is simple to install and operate and which reacts to a position change of a conduit relative to a vessel input.

In keeping with these objects and with others which will become apparent hereinafter, one feature of the present invention resides, briefly stated, in a safety device for blood-, wound secretion- or infusion supplying conduit leading to a vessel input, in which a magnet is mounted on the conduit and a Reed-relay is fixed near the magnet and is switched in the event of an increasing distance to the magnet during moving away of the vessel input, and as a result a monitoring device therefore releases an alarm signal, or a treatment device releases an alarm and interrupts its operation.

When the safety device is designed in accordance with the present invention, it eliminates the disadvantages of the prior art and provides for the above mentioned highly advantageous results.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

The single FIGURE of the drawings is a view schematically showing a safety device for blood-, wound secretion-, or infusion supplying conduit in accordance with the present invention.

DESCRIPTION OF THE PREFERRED EMBODIMENTS

A safety device for blood-, wound secretion- or infusion supplying conduit has a magnet 1 which is mounted on a hose of a canula or a catheter so as to be located close to the conduit leading to a vessel input, or is arranged at another location. A Reed-relay 2 formed as a protection contact relay with electromagnetic excitation is mounted independently and separately from the magnet 1.

The safety device in accordance with the present invention is further provided with a monitoring device or a corresponding treatment device which is identified with reference numeral 3.

During the operation of the safety device in accordance with the present invention when a distance to the magnet 1 is increased as a result of moving away of the vessel inlet from the vessel, the distance between the Reed-relay 2 and the magnet 1 is increased. If the device 3 is formed as a monitoring device, it produces an alarm in response to the increase of the distance between the Reed-relay 2 and the magnet. If the device 3 is formed as a corresponding treatment device, it reacts to the increased distance between the Reed-relay 2 and the magnet 1, for example by stopping a blood pump in dialysis apparatuses. Therefore, the safety device in accordance with the present invention eliminates the disadvantages of the existing devices with respect to safety risks and reliably reacts to a position change of the blood-, wound secretion- or infusion supply conduit relative to the vessel inlet.

It will be understood that each of the elements described above, or two or more together, may also find a useful application in other types of constructions differing from the types described above.

While the invention has been illustrated and described as embodied in a safety device for blood-, wound secretion- or infusion supplying conduit, and blood-, wound secretion or infusion supply system provided therewith, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A safety device for blood-, wound secretion and infusion supplying conduit which leads to a vessel inlet, the safety device comprising a magnet mountable on a conduit; a Reed-relay fixable substantially close to said magnet on a skin of a patient so that when a distance between said Reed-relay and said magnet increases as a result of moving away of the vessel inlet said Reed-relay is switched; and means for triggering alarm in response to the switching of said Reed-relay.

2. A safety device as defined in claim 1, wherein said magnet is arranged substantially close to the vessel inlet.

3. A safety device as defined in claim 1, wherein said means include monitoring means which monitors the distance between said Reed-relay and said magnet, and means for releasing the alarm in response to the switching of said Reed-relay.

4. A safety device as defined in claim 1, wherein said means include a treatment device which reacts when the distance between said Reed-relay and said magnet is increased, and means for releasing the alarm and interrupting its operation in response to the switching of said Reed-relay.

5. A blood-, wound secretion- and infusion supplying system comprising a blood-, wound secretion- and infusion supplying conduit adapted to lead to an inlet of a vessel; and safety device including a magnet mounted on said conduit, a Reed-relay fixable on the skin of a patient substantially close to said magnet so that when a distance between said Reed-relay and said magnet increases as a result of moving away of the vessel inlet said Reed-relay is switched, and means for triggering alarm in response to the switching of said Reed-relay.

6. A blood-, wound secretion- and infusion supplying system as defined in claim 5, wherein said magnet is arranged substantially close to the inlet of said vessel.

7. A blood-, wound secretion- and infusion supplying system as defined in claim 5, wherein said means include monitoring means monitors the distance between said Reed-relay and said magnet, and means for releasing the alarm in response to the switching of said Reed-relay.

8. A blood-, wound secretion- and infusion supplying system as defined in claim 5, wherein said means include a treating device reacts when the distance between said Reed-relay and said magnet is increased, and means for releasing the alarm and interrupting its operation in response to the switching of said Reed-relay.

\* \* \* \* \*